United States Patent [19]

Elsner

[11] 4,170,891
[45] Oct. 16, 1979

[54] POSITIONING CALIBRATION APPARATUS FOR TRANSDUCERS EMPLOYED IN NUCLEAR REACTOR VESSEL INSPECTION APPARATUS

[75] Inventor: Hans J. Elsner, Pittsburgh, Pa.

[73] Assignee: Westinghouse Electric Corp., Pittsburgh, Pa.

[21] Appl. No.: 805,546

[22] Filed: Jun. 10, 1977

[51] Int. Cl.² .......................................... G01N 29/04
[52] U.S. Cl. ...................................................... 73/1 R
[58] Field of Search .................... 73/1 R, 1 DV, 67.7, 73/67.8 R, 67.8 S, 71.5 VS; 310/335; 340/5 C, 8 FT

[56] References Cited

U.S. PATENT DOCUMENTS

| | | | |
|---|---|---|---|
| 2,394,461 | 2/1946 | Mason | 73/67.8 R X |
| 3,280,621 | 10/1966 | Cardinal et al. | 73/67.8 S |

FOREIGN PATENT DOCUMENTS 1300875 7/1962 France ..................................... 73/67.9

Primary Examiner—Charles A. Ruehl
Attorney, Agent, or Firm—L. A. DePaul; Z. L. Dermer

[57] ABSTRACT

Calibration apparatus for verifying the position and orientation of transducers used in nuclear reactor vessel inspection apparatus is disclosed. A tank, filled with water, the operating inspection medium, is fitted with a movable mounting assembly adapted to securely accommodate a transducer and the mounting assembly in which it is normally secured during an inspection procedure. The tank is also provided with a slidably mounted target positioned therein at a predetermined distance from the target which is selected to avoid the distortion effects in the near field of the transducer response. The calibration apparatus can be used to check the normal transducer mounting for either perpendicularity or angular orientation by moving the tank's mounting assembly via a lead screw with which it is threadingly engaged.

6 Claims, 14 Drawing Figures

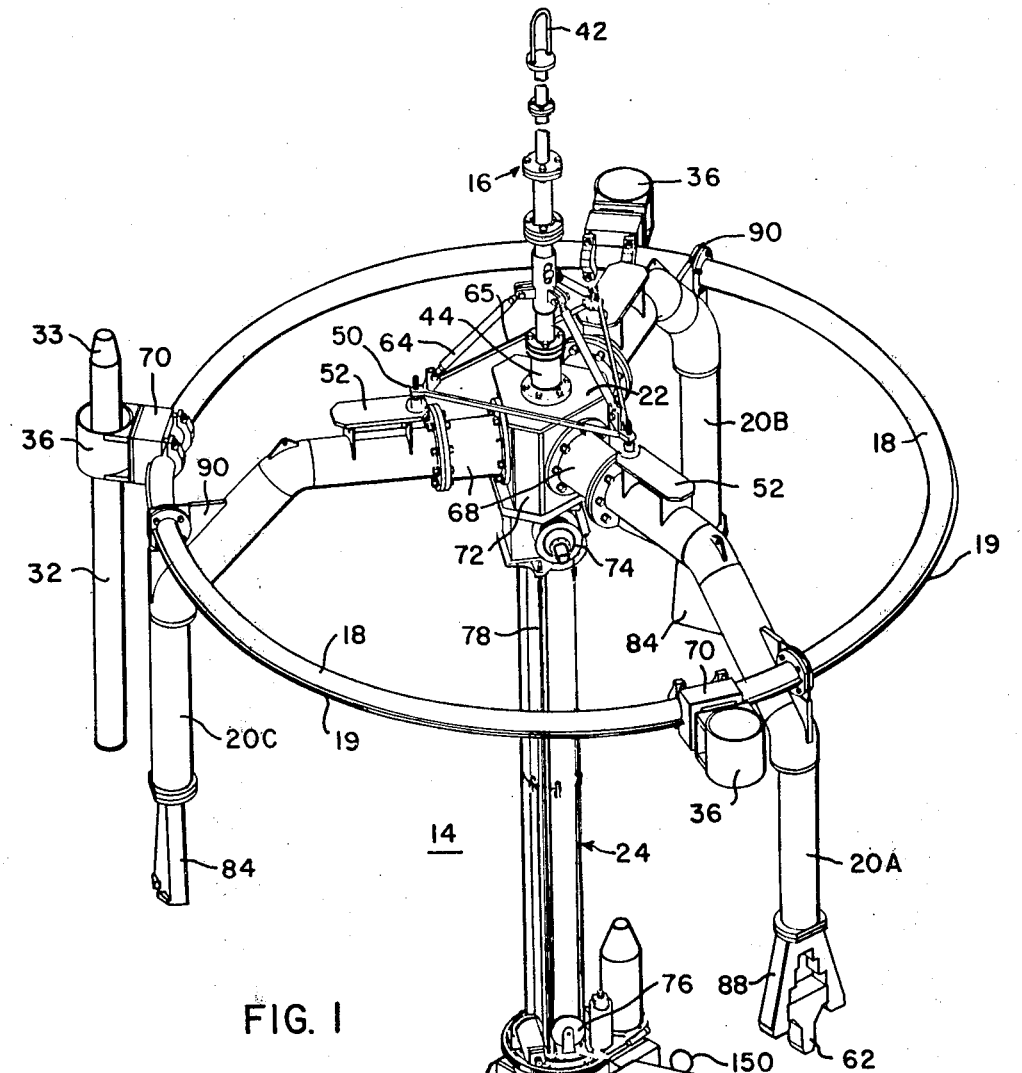
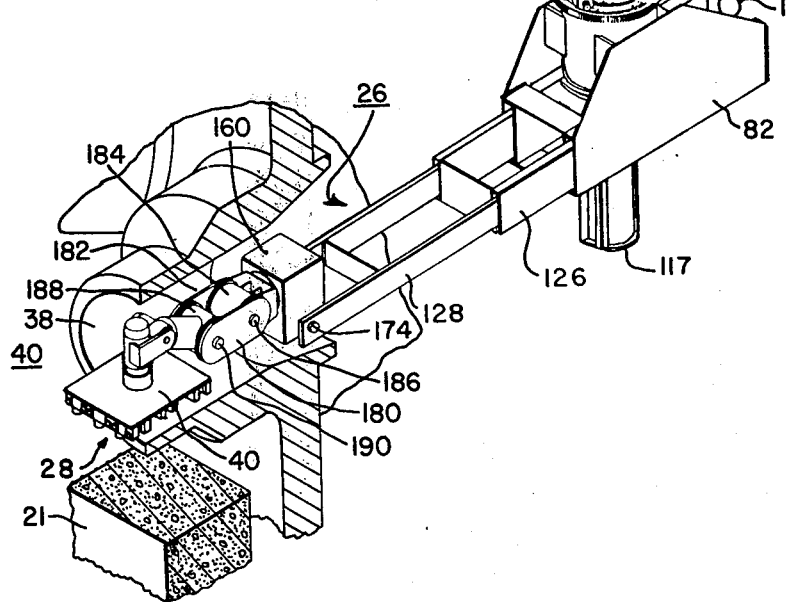
FIG. 1

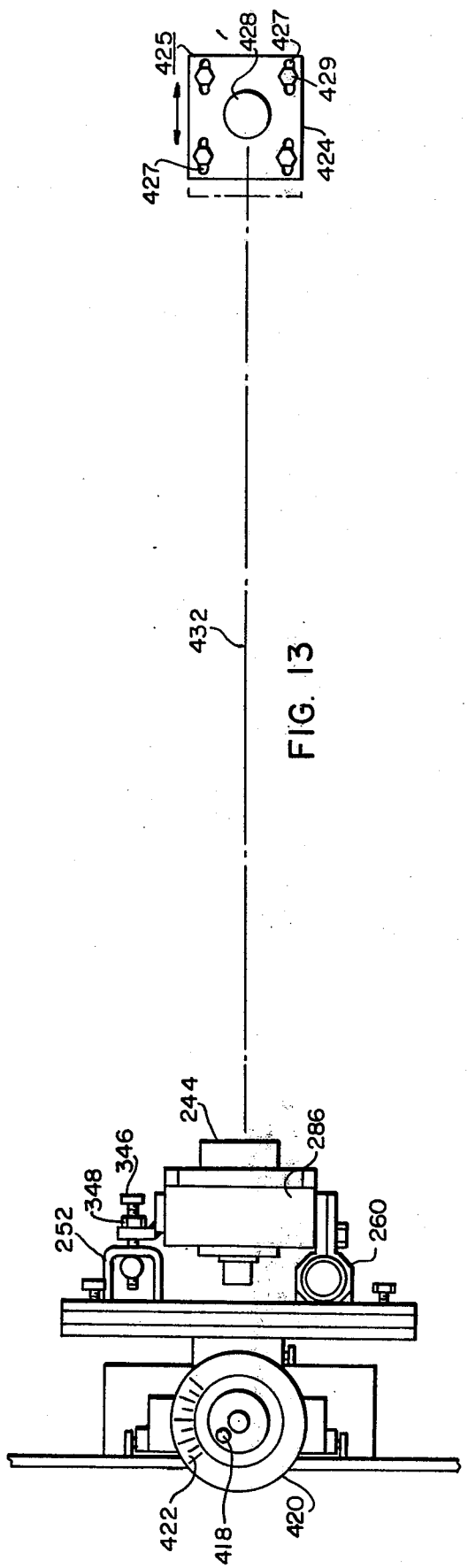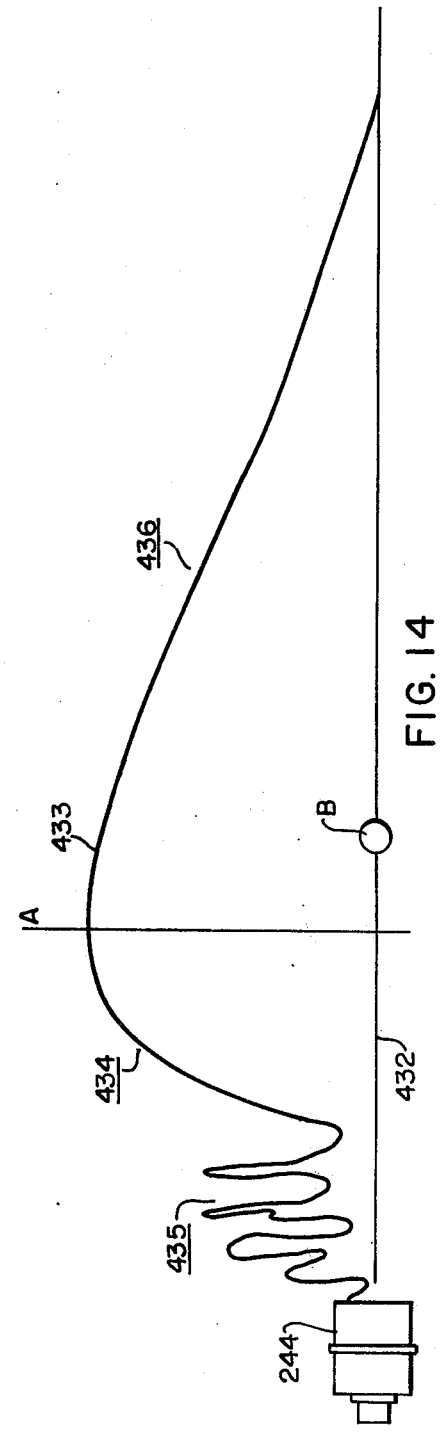

POSITIONING CALIBRATION APPARATUS FOR TRANSDUCERS EMPLOYED IN NUCLEAR REACTOR VESSEL INSPECTION APPARATUS

CROSS-REFERENCE TO RELATED APPLICATIONS

This application is hereby cross-referenced to the following patent applications which were filed on Mar. 25, 1977 and which are commonly assigned:

U.S. patent application Ser. No. 781,403 filed Mar. 25, 1977 entitled "Positioning Means For Circumferentially Locating Inspection Apparatus In A Nuclear Reactor Vessel", filed in the name of David C. Burns;

U.S. patent application Ser. No. 781,381 filed Mar. 25, 1977 entitled "Segmented Articulating Manipulator Arm for Nuclear Reactor Vessel inspection Apparatus", filed in the names of David C. Burns and Lanson Y. Shum;

U.S. patent application Ser. No. 781,380 filed Mar. 25, 1977 entitled "Variable Mounting Assembly For Transducers Employed In Nuclear Reactor Vessel Inspection Apparatus", filed in the names of Hans J. Elsner, Ronald F. Antol and Raymond P. Castner; U.S. patent application Ser. No. 781,390 filed Mar. 25, 1977 entitled "Pulley System Including Emergency Locking Means For Nuclear Reactor Vessel Inspection Apparatus", filed in the name of Renato D. Reyes;

U.S. patent application Ser. No. 781,401 filed Mar. 25, 1977 entitled "Emergency Braking System For Nuclear Reactor Vessel Inspection Apparatus", filed in the name of Renato D. Reys;

U.S. patent application Ser. No. 781,396 filed Mar. 25, 1977 entitled "Emergency Disconnect Means For The Manipulator Arm Of A Nuclear Reactor Vessel Inspection Apparatus", filed in the names of Arthur F. Jacobs and Duane W. Morris;

U.S. patent application Ser. No. 781,404 filed Mar. 25, 1977 entitled "Pressurized Cabling And Junction Boxes For Nuclear Reactor Vessel Inspection Apparatus", filed in the names of Charles V. Fields and Raymond P. Castner; and U.S. patent application Ser. No. 781,402 filed Mar. 25, 1977 entitled "Emergency Retraction Means For The Manipulator Arm Of A Nuclear Reactor Vessel Inspection Apparatus", filed in the names of Arthur F. Jacobs and Duane W. Morris.

Reference is also made to the commonly filed and assigned U.S. patent application Ser. No. 805,545 filed June 18, 1977 entitled "Calibration Assembly For Nuclear Reactor Vessel Inspection Apparatus", filed in the name of Hans J. Elsner.

All of the foregoing applications are hereby incorporated herein by reference.

BACKGROUND OF THE INVENTION

Nuclear reactor vessels employed in the commercial generation of electrical power are of two types; the pressurized water type or the boiling water type. In either case, the reactor vessel utilizes a generally cylindrical metallic container having a base and a top flange welded thereto. The main cylinder portion itself usually comprises a series of lesser cylinders welded to each other. In addition, a plurality of circumferentially spaced nozzles extend through the main cylinder wall and are welded thereto. Thus, numerous welds are necesssarily used in fabricating the reactor vessel, in mating the top flange to the main cylindrical body and in securing the inlet and outlet nozzles to the reactor vessel wall.

The reactor vessel, in use, is encased in a thick concrete containment area. However, the structural integrity of the reactor vessel, the concrete containment notwithstanding, due to the operating environment is of critical importance.

The weld areas of the reactor vessel are, of course, inspected prior to its initial use. Such inspection is carried out with all portions of the vessel relatively accessible to an inspection device prior to its encasement in the concrete containment. However, in-service inspection of the reactor vessel welds is not only desirable, but is mandated under governmental regulations.

Under such regulations, it is required that the vessel weld areas be subjected to periodic volumetric examination whereby the structural integrity of the vessel is monitored. Due to the nature of an in-service inspection, the device designed to accomplish the specified weld examinations must be capable of successfully operating in an underwater and radioactive environment under remote control while maintaining a high degree of control over the placement and movement of the inspection sensors.

The operating constraints are further complicated by the variety of reactor vessel sizes to which the inspection device must be able to be accommodated. Furthermore, the inspection device must not only be compatible with the weld placements of the reactor vessels now in use, but must also be sufficiently versatile to adapt to inspection duty in future vessels. In addition, the inspection device must be arranged in its use to have only minimal impact with normal refueling and maintenance operations.

The use of ultrasonic transducers to inspect metal welds is known. One such system is described in the periodical *Materials Evaluation*, July 1970, Vol. 28, No. 7, at pages 162–167. This article describes a transmitter-receiver type ultrasonic inspection system for use in the in-service inspection of nuclear reactor vessels. The positioning arrangement for the transducers uses a track which is mounted on the interior wall of the reactor vessel.

A method and apparatus for ultrasonic inspection of a pipe from within is disclosed in U.S. Pat. No. 3,584,504. In the apparatus disclosed therein, a transducer array is mounted on a carrier which is rotatable, by means of a central shaft of the apparatus, within the pipe.

In U.S. Pat. No. 3,809,607, a nuclear reactor vessel in-service inspection device is detailed, which device is adapted to permit remotely controlled and accurate positioning of a transducer array within a reactor vessel. This device comprises a positioning and support assembly consisting of a central body portion from which a plurality of radially directed support arms extend. The ends of the support arms are extended to and adapted for being seated on a predetermined portion of the reactor vessel to define a positional frame of reference for the inspection device relative to the reactor vessel itself. Repositioning and support assemblies are provided and include integral adjustment means which cooperate to permit the simultaneous variation of the extension of the support arms thereby allowing the inspection device to fit reactor vessels of differing diameters. A central column is connected to the positioning and support assemblies, which central column extends along the longitudinal axis thereof. One or more movable inspection assemblies are connected to the central column and include drive and position indicating means. Three specific inspection subassemblies include a flange scanner, a nozzle scanner and a vessel scanner. Each of these scanners employ multiprobe transmitter-receiver ultransonic transducers to permit more accurate volumetric plotting of the integrity of the welds used in fabricating the reactor vessel.

Since the development of the above-identified inspection devices, the original inspection code has been amended to call for more reliable and more rigorous inspections. In addition, these prior art devices were unable to accurately measure or reach certain weld areas of the reactor vessel. Still other drawbacks in the prior art inspection devices were the reliability and speed of the actual inspection effort.

One particular problem which was not solved by or in any of the above-described prior art devices was that of verifying the mounting of the transducers. It is necessary to insure that those transducers which were to be mounted perpendicularly were, in fact, so positioned and that those transducers which were to be mounted at predetermined angles to a transducer array plate were also, in fact, properly positioned. Without such mounting verification, the inspection results would be of little value.

SUMMARY OF THE INVENTION

Accordingly, there is provided calibration apparatus particularly suitable to verify the position and orientation of transducers used in nuclear reactor vessel inspection apparatus. The calibration apparatus includes movable mounting means adapted, within a tank, to removably secure a transducer mounted, in turn, in its normal inspection mounting.

Drive means which engage the movable mounting means are also provided for transporting the transducer in the tank to different positions relative to target means which are also provided. The target means is slidably positioned in the tank at a predetermined distance from the transducer, which distance is selected to avoid the distortion effects in the near field of the transducer response.

The drive means for the tank's mounting means is provided with graduated indicia of travel so that an operator can quickly determine by visual inspection the distance traveled by the mounting means. Alternatively, a scale can be affixed to or cut in the side of the tank to accomplish the same result.

BRIEF DESCRIPTION OF THE DRAWINGS

FIG. 1 is an isometric view of the nuclear reactor vessel inspection apparatus;

FIG. 13 is a top plan view of the mounting assembly and target employed in the calibration apparatus shown in FIG. 12; and FIG. 14 is a graphical representation of the near and far field effects in a transducer beam superimposed over the target distance shown in FIGS. 12 and 13.

DESCRIPTION OF THE PREFERRED EMBODIMENT

Figure 2:
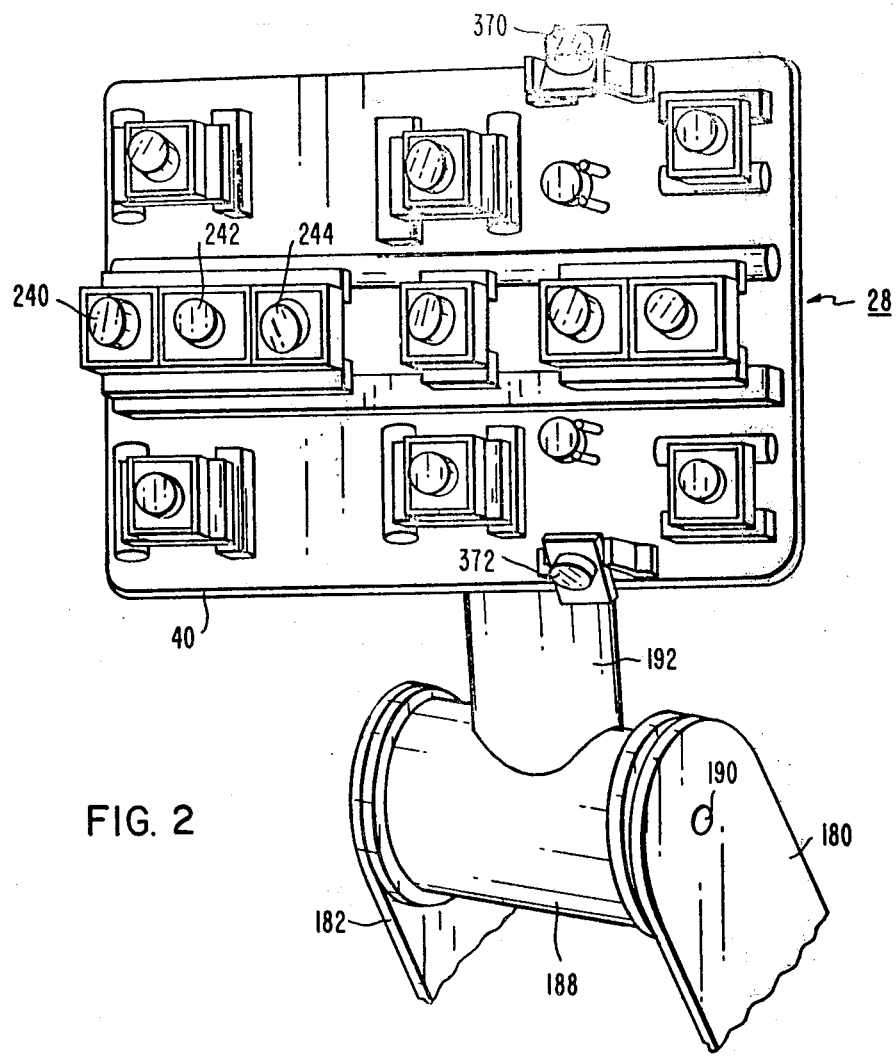
FIGS. 2 and 3 are isometric views of a transducer array utilized in the inspection apparatus shown in FIG. 1.

Referring now to the drawings wherein identical reference numerals have been used in the several views to identify like elements, FIG. 1 shows a perspective view of a nuclear reactor vessel inspection apparatus 14. The details of the inspection apparatus are set forth in all, but the last of the above cross-referenced United States Patent Applications and need not, therefore, be similarly described herein. If needed, such specific details thereof may be obtained by reference to any one of the cross-referenced applications, save the last; for example, U.S. patent application Ser. No. 781,380 filed Mar. 25, 1977.

For purposes of the present invention, it is sufficient to note that the inspection apparatus includes a quick-disconnect lifting assembly 16, a support ring 18, three support legs 20A, 20B and 20C, a head support assembly 22, a main column 24, a manipulator arm 26, a transducer array 28 and an overall control system 30 which includes an assortment of motors, resolvers and cabling. These main elements cooperate in a manner described in the cross-referenced applications to permit and facilitate inspection of a nuclear reactor vessel 10 in accordance with code requirements.

Figure 3:
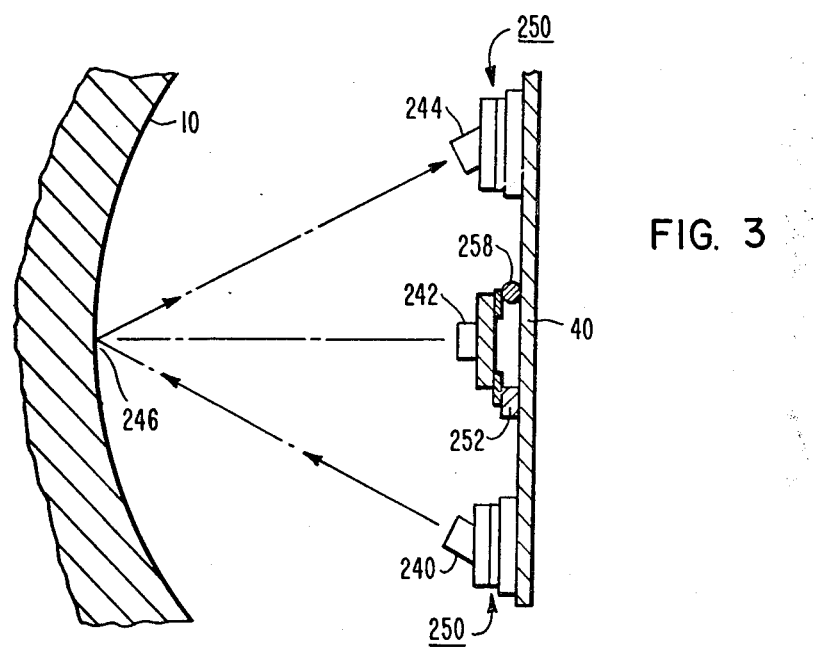

A transducer array 28 is employed as the examination means by which the integrity of the vessel welds or any desired portion of the vessel 10 can be inspected. A typical plan view of the transducer array 28 disposed on the mounting plate 40 is shown in FIG. 2. It should be noted with respect to the individual transducers themselves, that they are grouped or arrayed in a manner which permits the manipulator arms 26 to optimally position the plate 40 so that the greatest inspection flexibility results. For example, the three transducers 240, 242, and 244 can be positioned, as illustrated in FIG. 3, to direct their ultrasonic beams to impinge at point 246 on the vessel 10. Transducer 242 can be oriented to impinge perpendicularly to the vessel wall at point 246 to verify the water path distance or to check for vessel flaws. Transducers 240 and 244 can be used to direct angled beams at point 246 which may be a weld point or material adjacent thereto. Further, transducers 240 and 244 may be coupled to pitch-catch or merely echo their respective beams.

Figure 4:
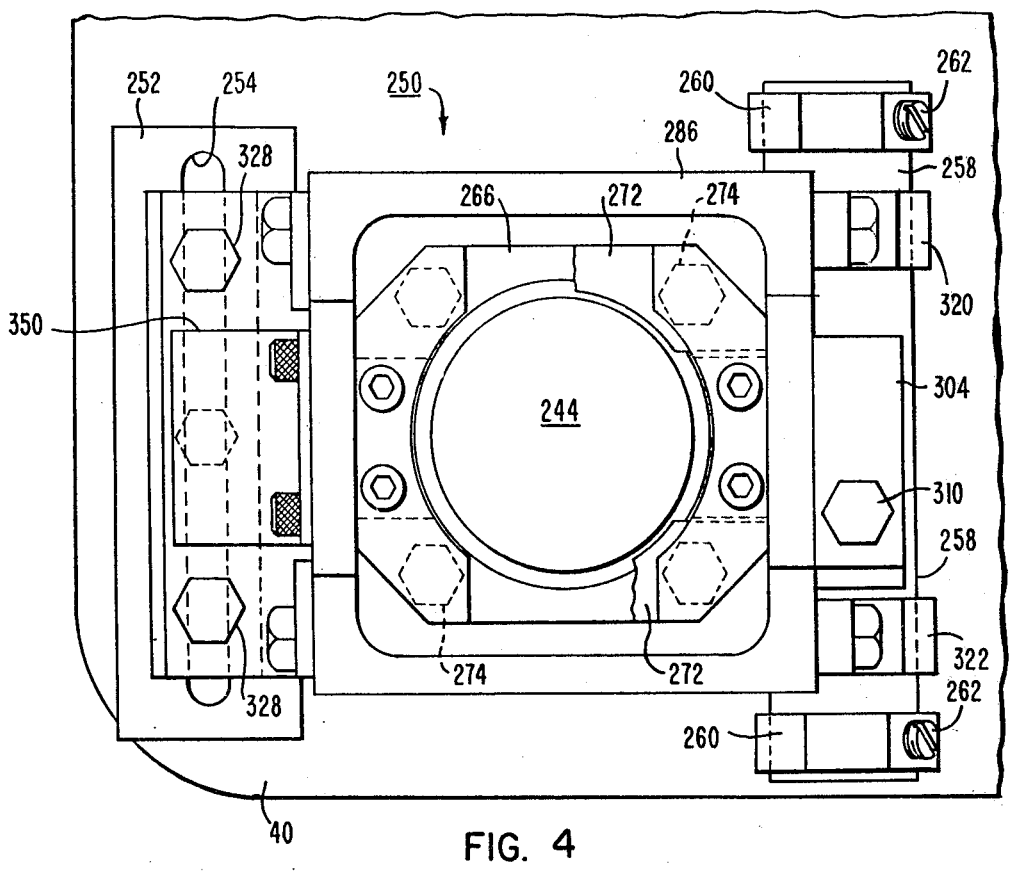
FIGS. 4 through 10 are plan or isometric views, some in partial section, illustrating the mounting assembly used to secure the transducers included in the array depicted in FIG. 2 during normal inspection procedures.
Figure 5:
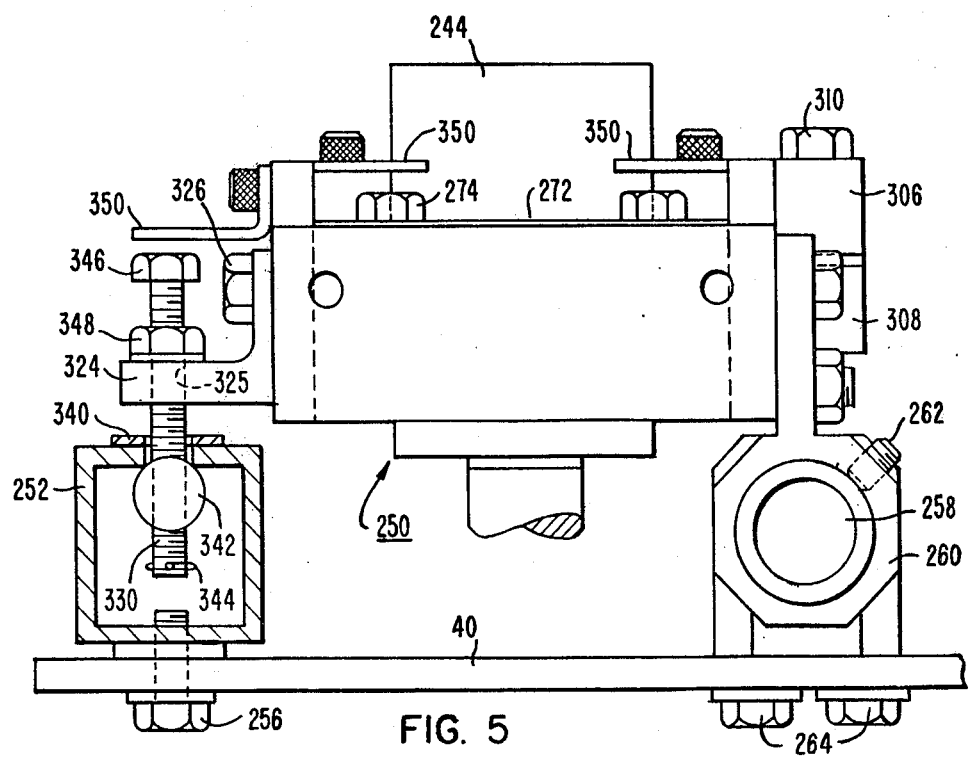

The individual transducers are secured to plate 40 by a transducer mounting assembly, generally designated 250, shown in FIGS. 4 and 5 in its normal orientation. The transducer mounting assembly includes a hollow, generally rectangularly shaped bar 252 having a slot 254 cut longitudinally therein. The bar 252 is bolted to the transducer plate 40 by bolts 256 one of which is shown in FIG. 5. A circular bar 258 is captured at either end thereof by holders 260 and fastened securely therein by set screws 262. The holders 260 are secured to the transducer plate 40 by bolts 264, also shown in FIG. 5, parallel to and spaced apart from bar 252.

A transducer 244 is held in a retaining block 266 having a circular bore 268 therein sized to accommodate the transducer 244. The top portion of bore 268 is countersunk or cut away to accept and support the flange 245 of transducer 244 in the circular shelf 270. Plates 272, which are fitted over and about the transducer flange 245 and secured to the top of retaining block 266 by bolts 274, tightly capture and retain the transducer 244 in the block 266. If necessary, the transducer 244 can be rotated in the retaining block by loosening the bolts 274. The retaining block 266 includes upstanding flanges 276 and 278 having circular bores 280 and 282 cut therethrough for respectively accepting a hinge pin 284 therein.

Figure 9:
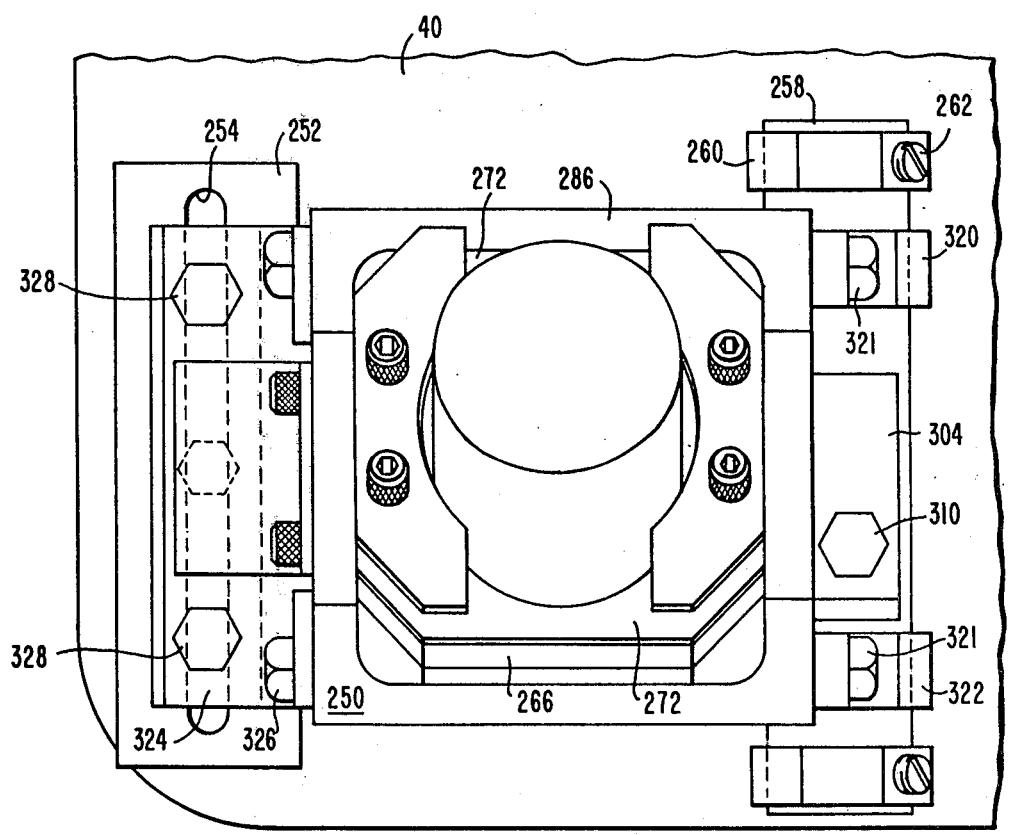
Figure 10:
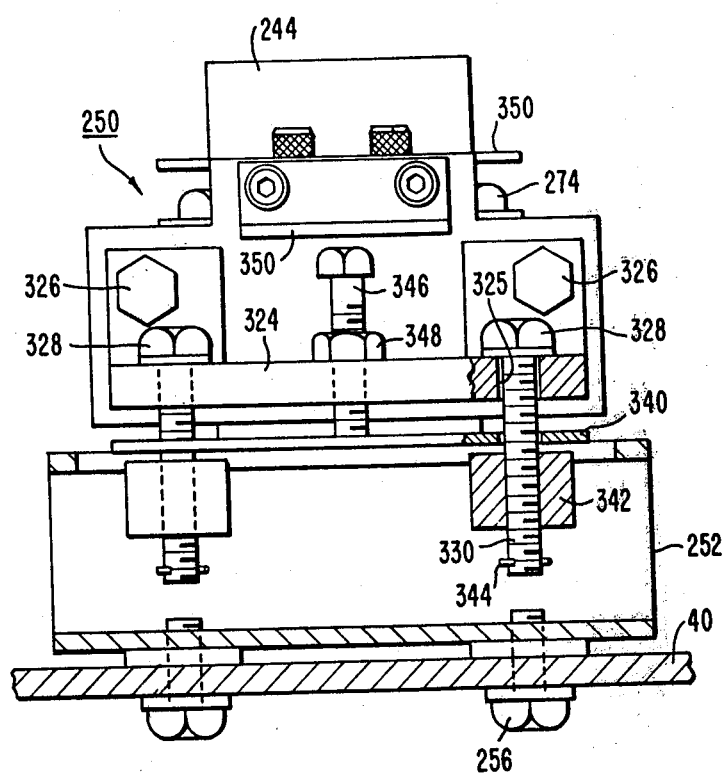
Figure 11:
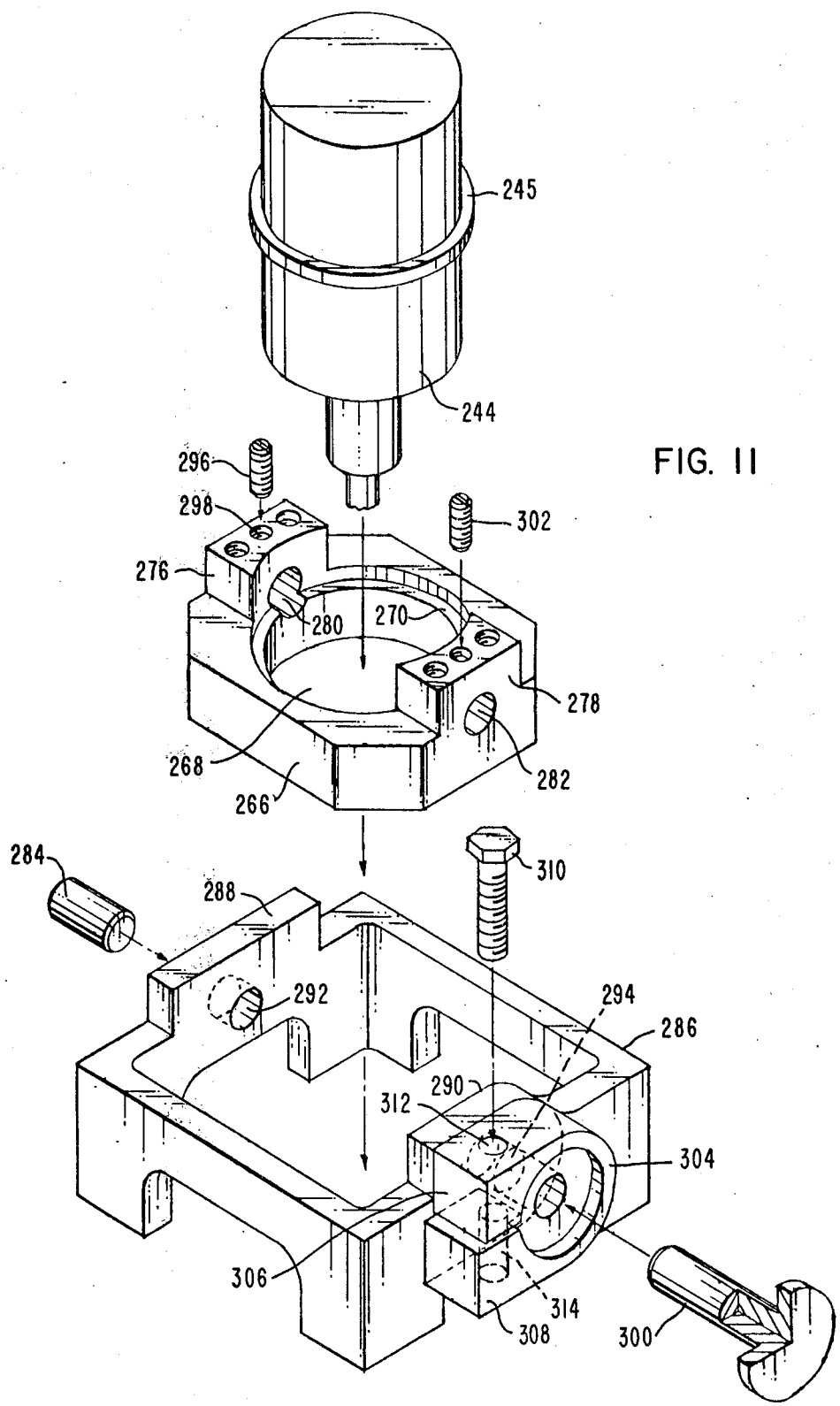
FIG. 11 is an exploded isometric view of the main portion of the mounting assembly shown in FIGS. 4 through 10.

The retaining block 266 is, in turn, secured to a yoke 286 which also includes two upstanding flanges 288 and 290, each having a circular bore 292 an 294 cut respectively therein. The hinge pin 284 extends through the bores 280 and 292 to pivotally fasten one side each of the block 266 and the yoke 286 to each other. A set screw 296, extending from the top of flange 276 through a bore 298 therein is used to clamp the hinge pin 284 to the retaining block 266. The other end of hinge pin 284 remains free to rotate in bore 292 of flange 288. The other side of retaining block 266 is also pivotally secured to the yoke 286 by a hinge pin 300, which is "T" shaped in cross-section. The leg of hinge pin 300 extends through the bores 282 and 294 of flanges 278 and 290 respectively. It is secured within bore 282 and clamped to flange 278 by a set screw 302. The head portion of hinge pin 300 abuts the flange 290 and is captured by a "U" shaped clamp 304 which is bolted to flange 290. The leg portions 306 and 308 of clamp 304 are held together by a bolt 310 which is threaded through bores 312 and 314 cut respectively in leg portions 306 and 308. When the bolt 310 is tightened down, leg portions 306 and 308 are drawn tightly together about the head portion of hinge pin 300 preventing it from turning in clamp 304. When bolt 310 is loosened, however, the transducer 244 and the retaining block 266 can be pivoted about the hinge pins 284 and 300. A side view of a pivoted restraining block 266, with transducer 244 having been tilted forwardly, is shown in FIG. 9. An exploded isometric view of the transducer 244, restraining block 266 and yoke 286 coupling is illustrated in FIG. 11.

As shown in FIGS. 4 and 9, two circular sleeves 320 and 322 are fit over and slid along the circular bar 258 prior to its being clamped into the holders 260. Th sleeves 320 and 322 are bolted to one side of the yoke 286 by bolts 321. An angle bracket 324 is secured to the other side of yoke 286 by bolts 326. The perpendicular portion of bracket 324 is bolted to the rectangular bar 252 by the end bolts 328. If bolts 328 are loosened, the yoke 286 and therefore the transducer 244 held therein can be moved transversely along the bars 252 and 258.

Figure 8:
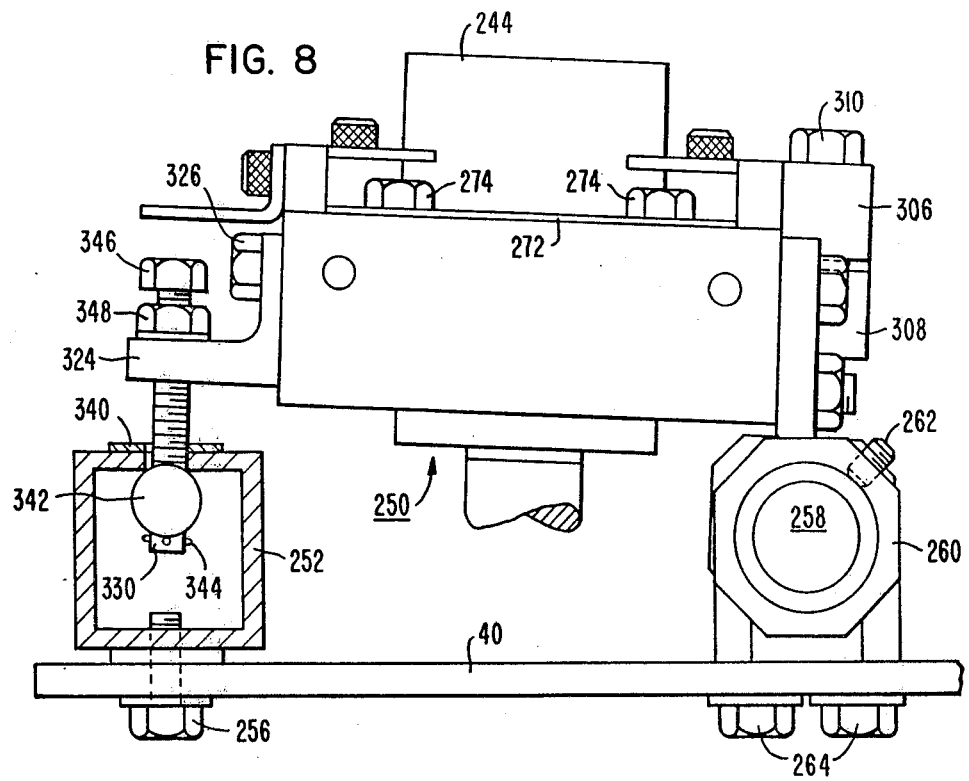

The bolts 328 pass through a bore 325 in the perpendicular portion of bracket 324 as illustrated in FIGS. 5, 8 and, most clearly, 10. After passing through the bore 325, the bolts extend through plate 340 and the slot 254 into the bar 252. The legs 330 of bolts 328 are threaded through the barrel nuts or pivots 342 and are pierced by cotter pins 344 at their terminal point to prevent their being worked out of the barrel nuts 342. A centered bolt 346 is threaded through the perpendicular portion of bracket 324 an abuts the plate 340 which acts as a stop therefor. When a locknut 348 is loosened, the bolt 346 can be tightened down, increasing the distance between plate 340 and the bracket 324, thereby pivoting the yoke 286 about the circular bar 258. An example of a pivoted yoke 286 is shown in FIG. 8. When the bolt 346 is tightened, the barrel nuts 342 pivot in the slot 254 permitting the yoke 286 to move to its canted position. It should be noted that the end bolts 328 are not loosened to effect or aid in this pivoting motion of the yoke 286. A number of bolt head flanges 350 are used to cover and retain various bolts should they loosen and work out of engagement.

Figure 6:
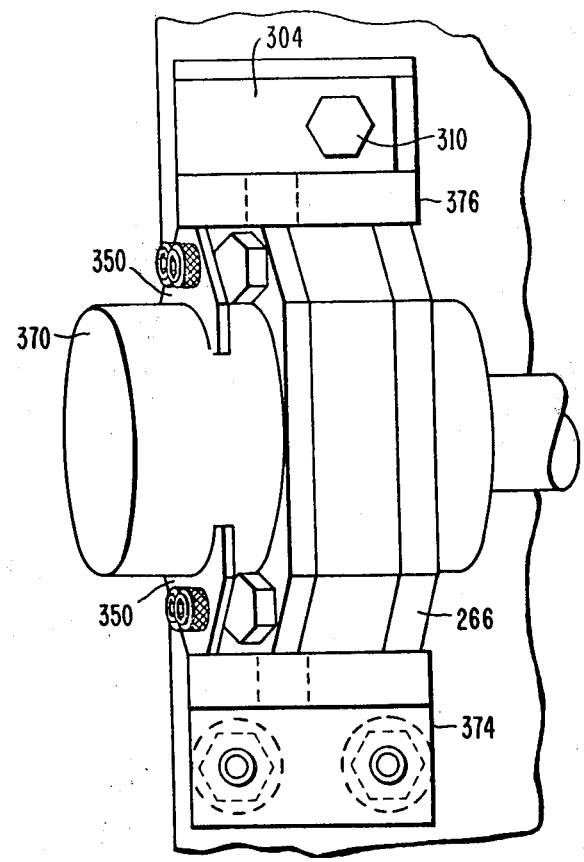
Figure 7:
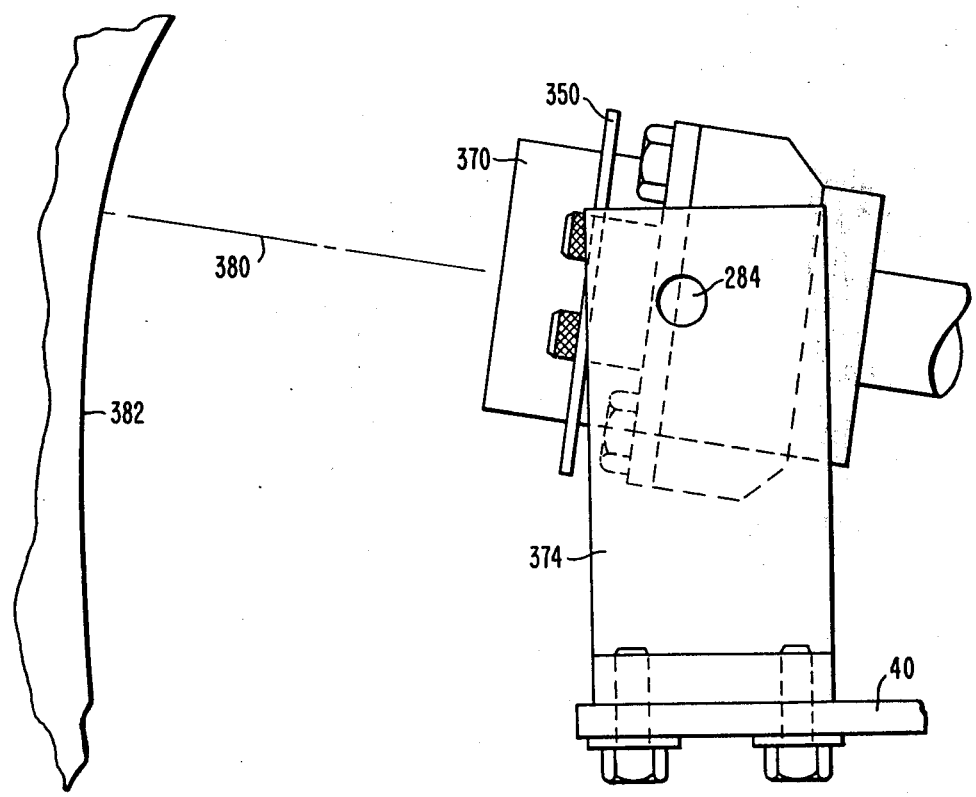

As the transducer array 28 is disposed about the vessel 10, particularly in or near one of the nozzles 38, it becomes difficult because of the curved vessel surfaces, to maintain one of the transducers perpendicular to the vessel wall and simultaneously insure proper clearances. For that reason, at least two transducers 370 and 372 are mounted on upstanding brackets 374 an 376 rather than on the bars 252 and 258. An example of this mounting arrangement is depicted in FIGS. 6 and 7. The restraining block 266 is removed from the yoke 286 and is bolted to the brackets 374 and 376. It is then pivoted at an appropriate angle by loosening bolt 310 of the "U" clamp 304 as previously described. In this case, however, clamp 304 is bolted to the block 266 rather than the yoke 286.

As shown in FIG. 7, the transducer beam 380 can be directed against the curved vessel wall 382, generally normal thereto, and the same transducer can be employed to receive the echo. Thus, the perpendicular distance between the transducer plate 40 and the vessel wall 382 can be continuously monitored. Utilizing such information, the manipulator arm 26 can be moved accordingly to prevent collisions.

Figure 12:
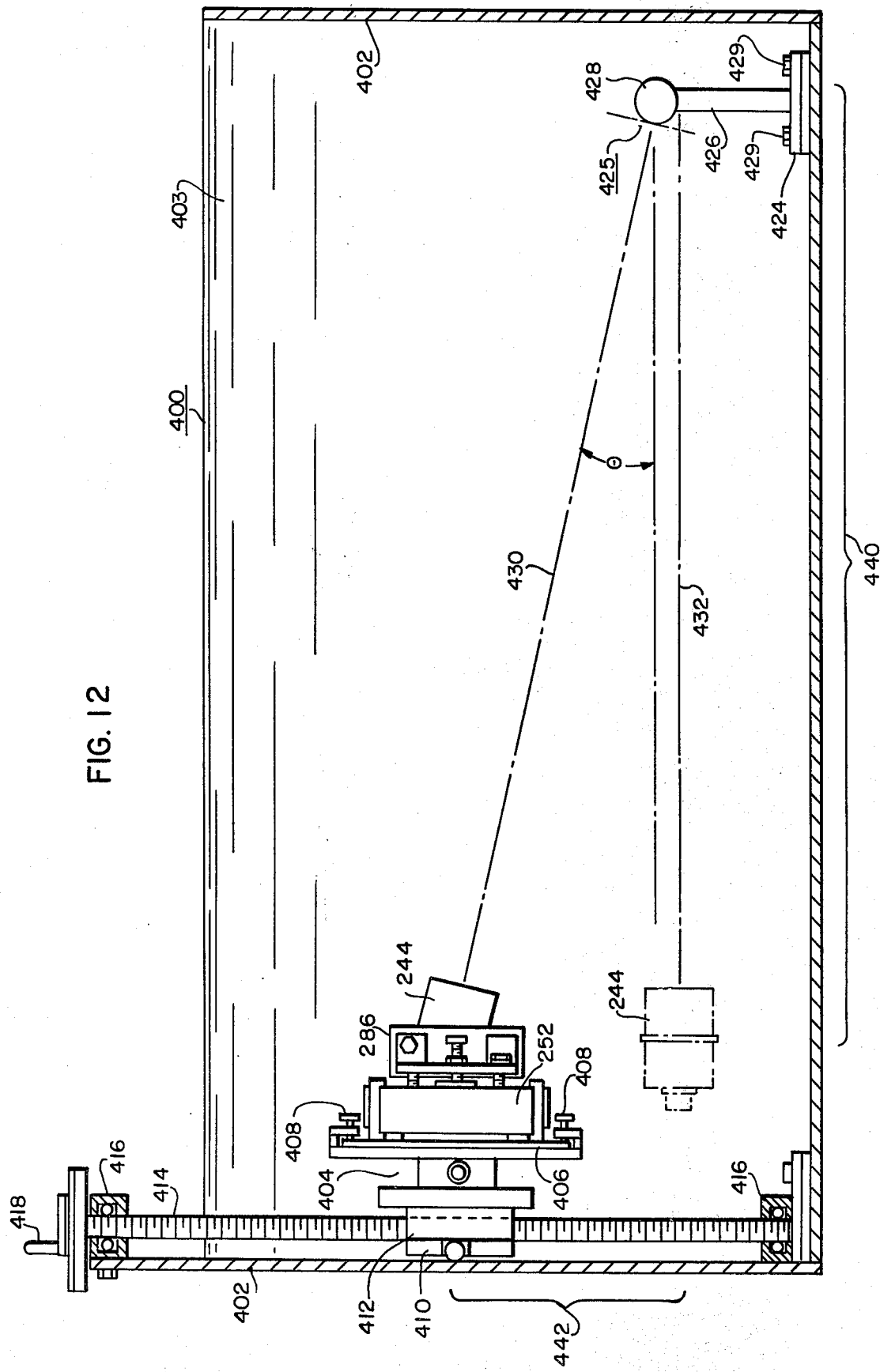
FIG. 12 is a schematic view of calibration apparatus, partly in phantom, in accordance with the present invention.

In order to insure that a given transducer will be properly oriented in its mounting assembly 250, calibration apparatus 400 as shown in FIG. 12 is used. Each transducer, secured in its retaining block 266 and yoke 286, as described hereinabove, is placed in a calibration tank 402 filled with water 403. The test transducer 244 is secured to a mounting assembly 404 which is movably mounted, in turn, within the calibration tank. The mounting assembly 404 generally comprises a rectangular bar 252 ad a circular bar 258 and the necessary bolts to secure the yoke 286 as if found on the transducer plate 40 and shown most clearly in FIG. 13. The bars 252 and 258 are fixed to plate 406 which is, in turn, secured to the mounting assembly 404 by bolts 408.

The rear portion of the mounting assembly 404 includes a slide block 410 having a threaded aperture 412 therein. Slide block 410 is engaged by a lead screw 414 which is rotatably clamped to the top and bottom portions of the calibration tank by the blocks 416. Th top portion of the lead screw 414 terminates in a handle or crank 418 which, when turned, will raise or lower the mounting assembly 404. Intermediate the handle 418 and the top of lead screw 414 is a collar 420, the top portion of which is graduated into a scale 422. The operator can use the scale 422 to determine the vertical travel of the mounting assembly 404. Alternatively, the side of the tank 402 can be fitted at approximately position 423, see FIG. 12, with a linear scale or rule (not shown) for the same purpose.

A target assembly 425 is positioned at the far end of tank 402. The target assembly comprises a base 424 having longitudinal slots 427 cut therein. The base 424 is secured to the tank 402 by bolts 429 and can be moved towards or away from the transducer by loosening the bolts 429 and sliding the base in an appropriate direction as shown in FIG. 13. Secured to the base 424 is a support or stand 426, having a generally rectangular cross-section, and secured, in turn, to the support 426 is a ball 428. As shall be hereinafter explained, the support 426 acts as a relatively infinitely large reflecting surface and the ball 428 acts as a relatively infinitely small reflecting surface.

The target assembly 425 is positioned at a predetermined distance from the mounting assembly 404 and the transducer 244 being calibrated. This distance is selected to avoid the distortion 435 found in the "near field" 434 of the transducer beam 432. Therefore, the target assembly 425 is positioned, as shown in FIG. 14, at a point B which is in the "far field" 436 of the transducer beam 432. Line A, drawn through the graphical representation of the transducer beam 432 shown in FIG. 14 which is superimposed over the beam transmission distance, separates the near and far fields. Point B, the location of the target assembly 425, is selected to be beyond the knee of the beam transmission curve 433 at a segment thereof which is generally linear and free of distortion. This insures that the calibration procedure will not be affected by the "near field" distortion.

In operation, the calibration apparatus 400 is utilized in the following manner. A transducer 244 to be calibrated is placed in its normal inspection mounting, as described hereinabove, in the calibration mounting assembly 404. The transducer 244 is then driven by turning handle 418 to a point, shown in phantom in FIG. 12, where it faces the support 426. When actuated in this position, transducer beam 432 impinges the support 426 in a generally perpendicular manner. The operator, who can track the reflected beam by appropriate equipment (not shown) can reach into the tank 402 and, by loosening the approrpiate bolt, nut or screw, adjust the transducer position to achieve a maximum reflection to coarsely verify perpendicularity. After such coarse adjustment has been made, the transducer 244 is moved up to where its beam will directly impinge the surface of ball 428. Since only one point on the ball's curved surface will reflect back a maximum beam, i.e., no scattering due to nonperpendicular impingement, fine positioning of the transducer 244 can now be accomplished by adjusting its position as needed to obtain such maximum reflection. In this manner, any transducer yaw offset can be corrected.

If the transducer 244 is to be mounted at a predetermined angle in the array 28, then its perpendicularity is checked as above, in alignment with the support 426 and the ball 428. The transducer 244 is moved upwardly from a zero point determined by the beam impingement with the ball 428. The mounting angle is designated as $\theta$ in FIG. 12. Since the distance from the ball 428 to the transducer 244 at the zero point is known or can be measured the transducer 244 is raised by an amount which corresponds by trigonometric function or relationship to the tangent of the angle $\theta$; that is, the horizontal distance 440 at the zero point, which is known, divided into the vertical distance 442 over which the transducer 244 is moved, which distance is also known. With the transducer raised to its solid line position in FIG. 12, adjustment of its position is made with respect to the ball 428 until a maximum reflection of beam 430 is received. At that point, the transducer is correctly oriented at the desired angle and it is secured in its mounting by the operator. The transducer 244 in its normal inspection mounting is then transferred to the array plate 40 and secured thereto as described above.

If necessary, the target assembly 425 can be positionally adjusted to alter the distance 440 by loosening the bolts 429. This capability is provided to insure that the target assembly will be in the "far field" of the transducer beam or that slight adjustments can be made in the geometry of the triangle formed by the transducer 244, the target assembly 425 and the zero point (distance 440).

While the invention has been shown and described herein in considerable detail, such disclosure is to be considered as only illustrative or exemplary in character and not restrictive, as within the broad scope of the invention, obvious modifications of or alternatives thereto may readily suggest themselves to persons skilled in this art.

I claim:

1. Apparatus for use in positionally calibrating ultrasonic transducers movably mounted in an assembly therefor, said apparatus comprising:
    (a) a tank capable of holding fluid therein;
    (b) mounting means, movably mounted in said tank for securing a transducer and the transducer mounting therein;
    (c) means for moving said mounting means cooperatively coupled thereto; and
    (d) a base, a relatively infinitely large reflecting surface and a relatively infinitely small reflecting surface mounted in said tank, a predetermined distance from said mounting means, said distance being selected to be greater than the distance required to place said reflecting surfaces without the "near field" of the transducer beam.

2. The apparatus according to claim 1 wherein said base is slidably mounted to the floor of said tank.

3. The apparatus according to claim 1 wherein said mounting means includes a slide having a threaded bore and wherein said means for moving includes a lead screw which threadingly engages said bore.

4. The apparatus accordng to claim 3 wherein said means for moving additionally comprises a handle for turning said lead screw and a collar having indicia thereon indicative of the distance moved by said mounting means.

5. The apparatus according to claim 3 wherein said means for moving further comprises means for indicating the distance moved by said mounting means when said lead screw is turned.

6. Apparatus for use in positionally calibrating ultrasonic transducers movably mounted in an assembly therefor, said apparatus comprising:
    a tank capable of holding fluid therein;
    mounting means, movably mounted in said tank for securing a transducer and the transducer mounting therein;
    means for moving said mounting means cooperatively coupled thereto;
    a base slidably mounted to the floor of said tank;
    a support leg connected to said base, said support leg having at least one flat surface and positioned on said base so that said flat surface faces the transducer when mounted in said mounting means; and
    a sphere mounted atop said support leg a predetermined distance from said mounting means, said distance being selected to be greater than the distance required to place said sphere without the "near field" of the transducer beam.

* * * * *